United States Patent
Block et al.

(10) Patent No.: US 6,531,488 B1
(45) Date of Patent: Mar. 11, 2003

(54) METHOD OF TREATING NEURODEGENERATIVE DISEASES

(75) Inventors: Gilbert A. Block, Ardmore, PA (US); Per Wold-Olsen, Oldwick, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/763,557

(22) PCT Filed: Aug. 27, 1999

(86) PCT No.: PCT/US99/19654

§ 371 (c)(1), (2), (4) Date: Feb. 22, 2001

(87) PCT Pub. No.: WO00/12093

PCT Pub. Date: Mar. 9, 2000

Related U.S. Application Data

(60) Provisional application No. 60/098,481, filed on Aug. 31, 1998.

(30) Foreign Application Priority Data

Oct. 16, 1998 (GB) ............................... 9822698

(51) Int. Cl.$^7$ ..................... A61K 31/445; A61K 31/40; A61K 31/38; A61K 31/34
(52) U.S. Cl. ....................... 514/315; 514/408; 514/438; 514/461
(58) Field of Search ................................ 514/408, 315, 514/438, 461

(56) References Cited

U.S. PATENT DOCUMENTS

| 5,643,960 | A |  | 7/1997  | Breitner et al. |
| 5,840,746 | A |  | 11/1998 | Ducharme et al. |
| 5,877,173 | A |  | 3/1999  | Olney et al. |
| 6,025,395 | A |  | 2/2000  | Breitner et al. |
| 6,329,397 | B1 | * | 12/2001 | McClure et al. ............ 514/330 |

FOREIGN PATENT DOCUMENTS

WO      WO 93/24115      12/1993

OTHER PUBLICATIONS

Physician's Desk Reference, Supplement A, 1997, Pfizer Inc., ARICEPT (Donepezil Hydrochloride Tablets), pp. A75–A78, vol. 51.

* cited by examiner

*Primary Examiner*—T J Criares
(74) *Attorney, Agent, or Firm*—Curtis C. Panzer; David L. Rose

(57) ABSTRACT

The present invention provides a method of treating a neurodegenerative disease, and in particular Alzheimer's disease, Mild Cognitive Impairment or other objective memory impairment which comprises the co-administration of ARICEPT or other cholinesterase inhibitor or cholenergic angonist and an effective amount of a selective COX-2 inhibitor. Although a wide range of COX-2 inhibitors may be employed in combination with ARICEPT, there are preferred choices which are specifically set forth herein.

13 Claims, No Drawings

METHOD OF TREATING NEURODEGENERATIVE DISEASES

CROSS REFERENCE TO RELATED APPLICATIONS

This application is a U.S. National Phase application under 35 U.S.C. §371 of PCT Application No. PCT/US99/19654, filed Aug. 27, 1999, which claims priority under 35 U.S.C. §119 from U.S. Provisional Application Serial No. 60/098,481, filed Aug. 31, 1998.

BACKGROUND TO THE INVENTION

ARICEPT ((±)-2,3-dihydro-5,6-diomethoxy-2-[[1-(phenylmethyl)-4-piperidinyl]methyl]-1H-indene-1-one hydrochloride), is currently prescribed for the partial relief of congitive sytmptoms associated with Alzheimer's disease. See, for example, pages 2161 to 2164 of the 1998 Pysician's Desk Reference (PDR). As stated therein, there is no evidence that donepezil (ARICEPT) or other cholinesterase inhibitors marketed for the treatment of Alzheimers Disease (e.g. EXELON, COGNEX) alter the course of the underlying dementing process.

The use of selective Cyclooxygenase-2 (COX-2) inhibitors have been disclosed for the treatment of Alzheimer's disease. See, for example, U.S. Pat. No. 5,474,995, U.S. Pat. No. 5,643,960, U.S. Pat. No. 5,604,260 and U.S. Pat. No. 5,436,265.

The present invention provides a method of treating a neurodegenerative disease and in particular Mild Cognitive Impairment and Alzheimer's disease which comprises the co-adminsitration of ARICEPT, or other cholinesterase inhibitors, and a selective COX-2 inhibitor.

In sharp contrast with ARICEPT administered alone, the co-administration of ARICEPT and a selective COX-2 inhibitor provides symptomatic relief of cognitive impairment and prevents future decline.

SUMMARY OF INVENTION

The present invention provides a method of treating a neurodegenerative disease, and in particular Alzheimer's disease, which comprises the co-administration of ARICEPT and a selective COX-2 inhibitor. Although a wide range of COX-2 inhibitors may be employed in combination with ARICEPT, there are preferred choices which are specifically set forth below.

DETAILED DESCRIPTION OF THE INVENTION

In one aspect the invention encompasses a method of treating a Mild Cognitive Impairment in a human which comprises co-administering to said human an effective amount of a cholinesterase inhibitor such as ARICEPT, or other cholinesterase inhibitors; or a cholenergic receptor agonist and an effective amount of a selective COX-2 inhibitor.

In a second aspect the invention encompasses a method of treating an objective memory impairment in a human which comprises co-administering to said human an effective amount of a cholinesterase inhibitor such as ARICEPT, or other cholinesterase inhibitors, or a cholenergic receptor agonist and an effective amount of a selective COX-2 inhibitor.

In a third aspect the invention encompasses a method of treating a Alzheimer's disease in a human which comprises co-administering to said human an effective amount of a cholinesterase inhibitor such as ARICEPT, or other cholinesterase inhibitor, or a cholenergic agonist and an effective amount of a selective COX-2 inhibitor.

For purposes of this specification a compound is said to be a selective COX-2 inhibitor if it possesses an IC50 for inhibiting COX-1 that is at least 200 greater than it's IC50 for inhibiting COX-2 in the assay set forth below.

For purposes of this specification, Mild Cognitive Impairment is defined as objective memory impairment below an age-appropriate norm on the Reye Auditory Verbal Learning Test, Selective Reminding Test, the Weschler Logical Memory Test or other objective memory test.

For purposes of this specification, Alzheimer's disease is defined in accordance with the NINLDS/ADRDA criteria or DSM-IV criteria.

ARICEPT, an example of a cholinesterase inhibitor administered alone, has been shown to be effective for the treatment of the symptoms Alzheimer's disease by the results of double blind, placebo-controlled clinical investigations in patients with Alzheimer's disease (diagnosed by NINCDS and DMS III-R criteria, Mini-Mental State Examination$\geq 10$ and $\leq 26$ and Clinical Demintia Rating 1 or 2). The effectiveness of ARICEPT in improving cognitive performance was assessed with the cognitive subscale of the Alzheimer's Disease Assessment Scale (ADAS-cog) and the CIBIC (Clinical Interview Blinded Investigation of Change). The ADAS-Cog examines selected cognitive performance including elements of memory, orientation, attention, language, and praxis. The ADAS-cog scoring is from 0 to 70, with higher scores indicating greater cognitive impairment. Elderly normal adults may score as low as 0, but it is not unusual for non-demented pateints to score slightly higher. The CIBIC is a global assessment of change conducted in a blinded fashion.

The preferred dosage of ARICEPT will be 5 or 10 mg, once or twice a day.

The preferred dosage range for the selective COX-2 inhibitor will be 1 to 400 mg once or twice a day. The preferred dosage may be 1, 5, 10, 12.5, 25, 50, 75, 100, 120, 150, 200, 250, or 400 mg once or twice a day.

The selective COX-2 inhibitors of this invention are most aptly those which are brain penetrant so that the concentration of COX-2 inhibitor, after administration of an effective dose for Alzheimer's disease, is at least the binding IC50 value and preferably at least 10 times that value, for example at least 100 times the binding IC50 value.

Among the selective COX-2 inhibitors, the following are preferred:

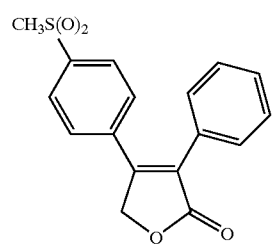

1

-continued

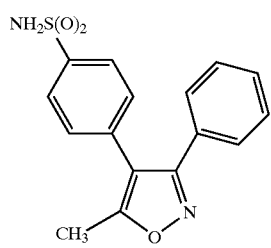

2

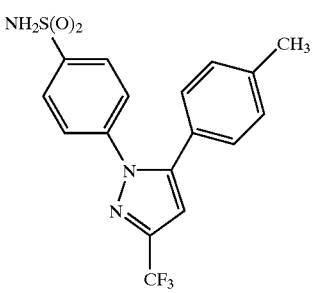

3

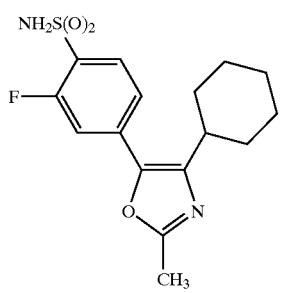

4

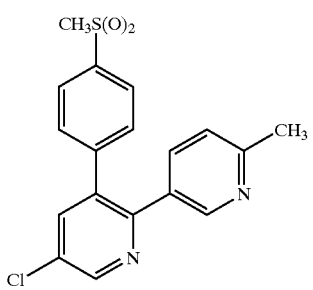

5

For Compound 1, the preferred dosage will be 12.5 or 25 mg total daily dose.

For Compound 5, the preferred dosage will be 10, 25, 50, 75, 100, 120 or 150 mg total daily dose.

ARICEPT or other cholinesterase inhibitor or cholenergic receptor agonist and the selective COX-2 inhibitor may be administered at the same time, or together in a single dosage, or at separate times during the day.

These compounds and their method of preparation are disclosed in the following patent documents, which are hereby incorporated by reference: U.S. Pat. No. 4,895,841, issued Jan. 23, 1990; U.S. Pat. No. 5,474,995, issued Dec. 12, 1995; U.S. Pat. No. 5,633,272, issued May 27, 1997; U.S. Pat. No. 5,521,207, issued May 28, 1996; 2183645 published Jun. 6, 1996 and WO 98/03484, published Jan. 29, 1998.

Oral administration (such as by tablet or capsule) is a preferred mode of administration In a fourth aspect, the invention encompasses pharmaceutical compositions for treating an objective memory impairment, comprising a pharmaceutically acceptable carrier and a non-toxic therapeutically effective amount of ARICEPT or other cholinesterase inhibitor or cholinergic agonist and an effective amount of a selective COX-2 inhibitor compound as defined herein.

In a fifth aspect, the invention encompasses pharmaceutical compositions for treating Mild Cognitive Impairment, comprising a pharmaceutically acceptable carrier and a non-toxic therapeutically effective amount of ARICEPT or other cholinesterase inhibitor or cholenergic agonist and an effective amount of a selective COX-2 inhibitor compound as defined herein.

In a sixth aspect, the invention encompasses pharmaceutical compositions for treating Alzheimer's Disease, comprising a pharmaceutically acceptable carrier and a non-toxic therapeutically effective amount of ARICEPT cholinesterase inhibitor or cholenergic agonist and an effective amount of a selective COX-2 inhibitor compound as defined herein.

The pharmaceutical compositions of the present invention comprise ARICEPT, or other cholinesterase inhibitors, and a selective COX-2 inhibitor as the active ingredients and may also contain a pharmaceutically acceptable carrier and optionally other therapeutic ingredients.

COX-2 selectivity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a putative selective COX-2 inhibitor. The $IC_{50}$ values represent the concentration of inhibitor required to return $PGE_2$ synthesis to 50% of that obtained as compared to the uninhibited control.

For the treatment of Mild Cognitive impairment or other objectives memory impairment, or Alzheimer's Disease, ARICEPT and the selective COX-2 inhibitors of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

ARICEPT or other cholinesterase inhibitor or cholenergic agonist and an effective amount of a selective COX-2 inhibitors of the invention may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The amount of active ingredient that may be combined with the carrier materials to produce a single dosage form will vary depending upon the host treated and the particular mode of administration. For example, a formulation intended for the oral administration of humans may contain from 5 mg to 500 mg of active agent compounded with an appropriate and convenient amount of carrier material which may vary from about 5 to about 95 percent of the total composition. Dosage unit forms will generally contain between from about 5 mg to about 500 mg of an active ingredient, typically 5, 10, 12.5, 25 mg, 50 mg, 75 mg, 100 mg, 120 mg, 150 mg, 200 mg, 300 mg, 400 mg or 500 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The present invention provides a method of treating a neurodegenerative disease and in particular Alzheimers disease which comprises administering to a human in need thereof a therapeutically effective amount of a non-steroid COX-II inhibitor.

From another aspect this invention provides the use of a COX-2 inhibitor in the manufacture of a medicament for the treatment of neurodegenerative diseases including dementia, and in particular Alzheimers disease. Risk factors include those based on Apo lipoprotein genotype, age, presence of Mild Cognitive Impairment and family history.

When used herein the term "treating" includes treatment of existing disease and prophylactic treatment of those at risk of developing the disease.

The selective COX-2 inhibitor may be of any structural type other than a steroid. However, most aptly the selective COX-2 inhibitor employed in this invention is not a carboxylic acid or a salt thereof. Most favourably it will possess a $SO_2CH_3$, $NHSO_2CH_3$, $SO_2NH_2$, $SO_2NHCH_3$ or like substituent on an aromatic ring especially on a phenyl ring.

The invention also provides the use of such compounds in the manufacture of a medicament for the treatment of neurodegenerative disease and in particular Mild Cognitive Impairment and Alzheimer's disease.

It is a great advantage of this invention that treatment may be carried out without causing gastric side effects of the type that can occur when COX I inhibitors are used for prolonged periods. Since neurodegenerative diseases such as Alzheimers disease are generally progressive, treatment may need to take place for a number of years. Thus the provision of medicaments which are effective without any significant tendency to cause gastric side effects at the therapeutic dose is of great use particularly to the elderly. The use of medicaments of this invention for the treatment of patients who are asymptotic is also envisaged especially in those cases where genetic information suggests that the patient is likely to develop Alzheimer's disease or other neurodegenerative disease especially those which may be termed dementia, for example senile dementia or pre-senile dementia.

Favourably this invention provides a method of treating neurodegenerative disease without any significant tendency to cause gastric side effects which comprises the oral administration of a pharmaceutical composition which comprises an effective amount of a COX-2 inhibitor and a pharmaceutical acceptable carrier therefor.

Such a method is applicable to patients with overt symptoms of disease and is applicable without overt symptoms of the disease (asymptotic patients).

EXAMPLE

Using PCR analysis of mRNA extracted from the post-mortem hippocampus of 7 AD patients and 6 age-matched control patients (with no history of neurological or neuropsychiatric diseases, we found COX-II mRNA in 6 AD patients. Four of the control patients showed no COX-II mRNA. In situ hybridization histochemistry also showed COX-II mRNA in the hippocampus of 4 AD patients but not in 5 control patients. Western blot analysis of temporal lobe cortex showed COX-II protein in 3AD patients but not in 3 control patients.

These results show that COX-II is induced in the medial temporal lobe of AD patients, a brain region most severely affected during alzheimers disease process. The results indicate that the inflammatory condition associated with AD involve COX-II in its aetiology and show that treating AD patients with brain penetrant selective COX-II inhibitors will be effective.

Assays for Determining Biological Activity

The putative selective COX-2 inhibitors can be tested using the following assays to determine their cyclooxygenase-2 inhibiting activity.

Inhibition of Cyclooxygenase Activity

Compounds were tested as inhibitors of cyclooxygenase activity in whole cell and microsomal cyclooxygenase assays. Both of these assays measured prostaglandin $E_2$ ($PGE_2$) synthesis in response to arachidonic acid, using a radioimmunoassay. Cells used for whole cell assays, and from which microsomes were prepared for microsomal assays, were human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate addition. $IC_{50}$ values represent the concentration of putative inhibitor required to return $PGE_2$ synthesis to 50% of that obtained as compared to the uninhibited control.

What is claimed is:

1. A method of treating a Mild Cognitive Impairment in a human consisting essentially of co-administering to said human an effective amount of a cholinesterase inhibitor or a cholenergic receptor agonist and an effective amount of a selective COX-2 inhibitor.

2. A method according to claim 1 of treating a Mild Cognitive impairment in a human consisting essentially of co-administering to said human an effective amount of ARICEPT and an effective amount of a selective COX-2 inhibitor.

3. A method of treating a Mild Cognitive Impairment in a human consisting essentially of co-administering to said human 5 or 10 mg of ARECEPT, once or twice a day and an effective amount of a selective COX-2 inhibitor.

4. A method of treating a Mild Cognitive Impairment in a human consisting essentially of co-administering to said human an effective amount of a cholinesterase inhibitor or a cholenergic agonist and 5 to 400 mg of a selective COX-2 inhibitor once or twice a day.

5. A Method according to claims 1 wherein the selective COX-2 inhibitor is selected from

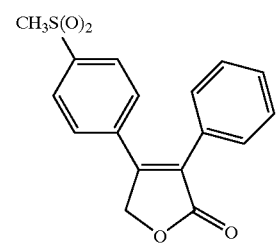

1

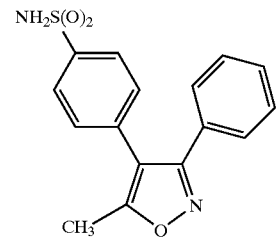

2

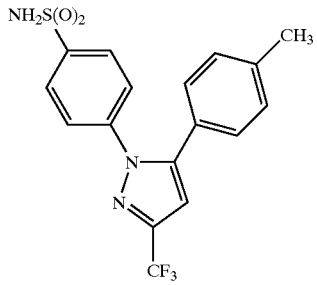

3

-continued

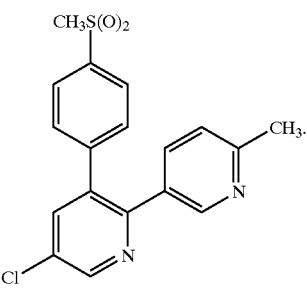

4

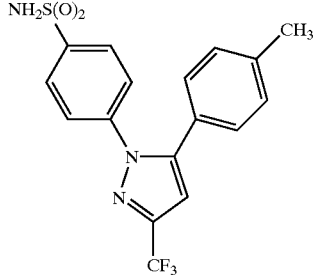

3

5

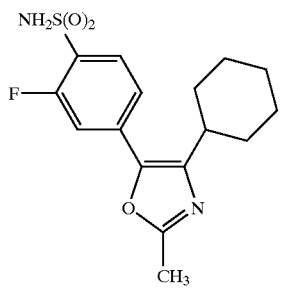

6. A method of treating Alzheimer's disease in a human consisting essentially of co-administering to said human an effective amount of a cholinesterase inhibitor or a cholenergic receptor agonist and an effective amount of a selective COX-2 inhibitor.

7. A method according to claim 6 of treating Alzheimer's disease in a human consisting essentially of co-administering to said human an effective amount of ARICEPT and an effective amount of a selective COX-2 inhibitor.

8. A method of treating Alzheimer's disease in a human consisting essentially of co-administering to said human 5 or 10 mg of ARECEPT, once or twice a day and an effective amount of a selective COX-2 inhibitor.

9. A method according to claims 7 wherein the selective COX-2 inhibitor is selected from 10. A method of treating a Mild Cognitive Impairment in a human consisting essentially of co-administering to said human 5 or 10 mg of ARECEPT, once or twice a day and 5 to 400 mg of a selective COX-2 inhibitor once or twice a day.

11. A method of treating Alzheimer's disease in a human consisting essentially of co-administering to said human 5 or 10 mg of ARECEPT, once or twice a day and 5 to 400 mg of a selective COX-2 inhibitor once or twice a day.

12. A pharmaceutical compositions for treating Mild Cognitive Impairment, consisting essentially of a pharmaceutically acceptable carrier and a non-toxic therapeutically effective amount of ARICEPT and an effective amount of a selective COX-2 inhibitor.

13. A pharmaceutical compositions for treating Alzheimer's Disease, consisting essentially of a pharmaceutically acceptable carrier and a non-toxic therapeutically effective amount of ARICEPT and an effective amount of a selective COX-2 inhibitor compound.

* * * * *